United States Patent [19]

Olsen

[11] Patent Number: 4,841,069

[45] Date of Patent: Jun. 20, 1989

[54] AMMONOLYSIS-ALKYLATION REACTIONS USING AMMONIA AND AN ALCOHOL TO PREPARE N-ALKYL MALEIMIDES AND N-ALKYL SUCCINIMIDES

[75] Inventor: Robert J. Olsen, Lisle, Ill.

[73] Assignee: Amoco Corporation, Chicago, Ill.

[21] Appl. No.: 31,545

[22] Filed: Mar. 30, 1987

[51] Int. Cl.$^4$ .............. C07D 207/408; C07D 207/452
[52] U.S. Cl. .................................. 548/545; 548/548
[58] Field of Search ...................... 548/513, 545, 548

[56] References Cited

U.S. PATENT DOCUMENTS

| | | | |
|---|---|---|---|
| 3,092,638 | 6/1963 | Liao et al. | 548/552 |
| 3,899,509 | 8/1975 | Riemenschneider | 548/548 |
| 3,910,951 | 10/1975 | Fuerst et al. | 548/545 |

Primary Examiner—David B. Springer
Attorney, Agent, or Firm—Reed F. Riley; William H. Magidson; Ralph C. Medhurst

[57] ABSTRACT

Ammonolysis-alkylation using a $C_1$ to $C_8$ alkanol and ammonia is used to prepare cyclic N-alkylated compounds in a one-step process. In the presence of hydrogen added as a reducing agent, a reduced N-alkylated compound can be formed.

13 Claims, No Drawings

AMMONOLYSIS-ALKYLATION REACTIONS USING AMMONIA AND AN ALCOHOL TO PREPARE N-ALKYL MALEIMIDES AND N-ALKYL SUCCINIMIDES

BACKGROUND OF THE INVENTION

This invention relates to the preparation of N-alkylated compounds by reaction of an organic diacid, diester, anhydride or a lactone with ammonia and an alcohol. More particularly, the invention relates to the one-step preparation of a cyclic N-alkylated compound, such as a N-alkylsuccinimide, from an organic diacid, diester, anhydride or lactone by reaction with ammonia and a $C_1$ to $C_8$ alkanol either added or formed in situ. The ammonolysis-alkylation may be thermal or catalyzed. In another aspect of the invention a cyclic N-alkylated compound is formed in the presence of a reducing agent such that reduction of the process feed is accomplished together with the ammonolysis-alkylation reaction.

Previous syntheses making the N-alkylated derivatives from such compounds as a dialkyl succinate, succinic acid, succinic anhydride or 4-butyrolactone were carried out stepwise by first making a metal salt of the corresponding imide and reacting the latter with an alkyl halide or directly employing the reaction of a primary amine with the oxygen-containing starting material. These techniques are either multistep and expensive or simply expensive because of the price of primary amines. In a search for a low-cost, simple technique for carrying out these and similar reactions, it has been found that ammonolysis-alkylation can be accomplished in a single step in a thermal or catalyzed reaction employing ammonia and an alkanol, the alkanol either added or generated by the reaction in situ. The new reaction is capable of high conversions and high selectivities to the desired N-alkylated products, a finding of major commercial significance.

In the past, N-alkylated compounds have been prepared from dialkylsuccinates by thermal reaction with a primary amine. See U.S. Pat. No. 2,643,257. Of interest also is a two-step process for their preparation. A compound containing an imide nitrogen is first reacted to form an alkali metal salt, for example, potassium phthalimide, which is then reacted with an alkyl halide. See, for example, Gibson, M. and Bradshaw, R., Angew. Chem. Int. Ed. 7,919 (1963). Related to the present invention is (1) imide and amide alkylation with alcohols, see O. Mitsunobu et al. JACS 94,679 (1972), E. White et al., JACS 87,5261 (1965) and V. Evgrasin, et al., Kinet. Katal, 14,440 (1973) and (2) the reaction of maleic anhydride with a primary amine. See, for example, U.S. Pat. No. 2,262,262 and British Pat. No. 1,123,515.

SUMMARY OF THE INVENTION

The invention described herein is a process comprising forming a first compound containing the

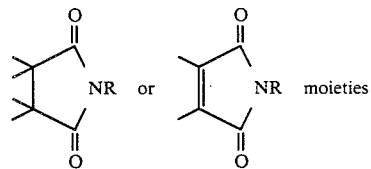

from a scond compound containing the

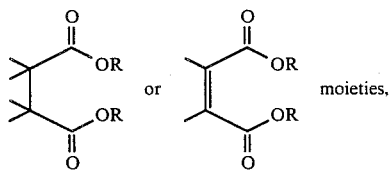

wherein R is H or a $C_1$ to $C_8$ alkyl radical, by contacting under reaction conditions said second compound with ammonia and the corresponding $C_1$ to $C_8$ alkanol.

In another aspect, the invention described herein is a process comprising forming a first compound containing the

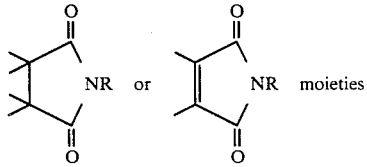

from a second compound containing the

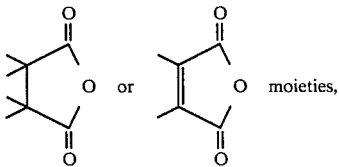

wherein R is a $C_1$ to $C_8$ alkyl radical, by contacting under reaction conditions said second compound with ammonia and the corresponding $C_1$ to $C_8$ alkanol.

In a third aspect, the invention described herein is a process comprising forming a first compound containing the

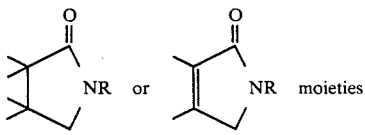

from a second compound containing the

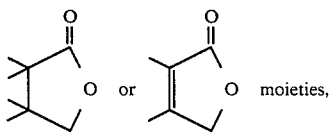

wherein R is a $C_1$ to $C_8$ alkyl radical, by contacting under reaction conditions said second compound with ammonia and the corresponding $C_1$ to $C_8$ alkanol.

In still another variant, the invention described herein relates to carrying out the above-described one step processes in the presence of hydrogen such that ammonolysis-alkylation and a reduction of the organic substrate are accomplished together.

DETAILED DESCRIPTION OF THE INVENTION

The feed for process of the instant invention can be a diacid such as maleic acid, succinic acid, phthalic acid and the like or substituted derivatives thereof. The diacid must be of the appropriate carbon number and capable of cyclizing in the reaction to form the N-alkylated compound. The alkyl diesters of such diacids are also useful. By alkyl is meant a $C_1$ to $C_8$ alkyl radical, such as the methyl, ethyl, isopropyl, butyl, isobutyl, pentyl, hexyl, heptyl and octyl radicals, more preferably, the methyl, ethyl and propyl radicals, and most preferably, the methyl radical. Anhydrides of such acids are also useful. Acids such as succinic and phthalic are preferred as are their anhydrides and their diesters, particularly their dimethyl or diethyl esters.

Lactones useful in the process of the instant invention include both saturated and unsaturated compounds, which compounds may or may not be alkyl or aryl substituted. In particular, butyrolactone is useful which may be produced either by Reppe chemistry or by hydrogenation of a maleic derivative. Formation of a N-alkylpyrrolidone starting with a maleic derivative and using ammonolysis-alkylation can form the basis of a particularly desirable process.

Additionally, ammonia and a $C_1$ to $C_8$ alkanol are also used in the process, the latter not being necessary in the event a diester is used which can form the corresponding alkanol in situ during the reaction. The alkanols which are preferred are methanol, ethanol and propanol, and methanol and ethanol are the most preferred alkanols.

The reaction of the substrate, ammonia and the $C_1$ to $C_8$ alkanol is carried out under a pressure of about near ambient pressure to about 200 atms., and more preferably, about 2 atms. to about 100 atms. The reaction temperature is suitably between about 80° C. and about 400° C., and more preferably, between about 100° C. and about 350° C.. Reaction times depend to some extent upon the pressure and the temperature employed but generally are in the range of about 0.25 hrs. to about 8 hrs., more preferably about 1 hr. to about 4 hrs. It has been found that longer reaction times are required for N-butyl compounds than are required for N-ethyl compounds. N-methyl derivatives appear to form most rapidly under equivalent reaction conditions. The reactions are conveniently carried out batchwise with agitation although a continuous process in a plug flow, tubular or other type of reactor is possible. The substrate can conveniently be added to the reactor as a mixture in the alkanol. The reactions can be carried out thermally or, if necessary with the addition of a catalyst.

In the slower reactions where the N-alkyl group is large, for example, where a $C_2$ to $C_8$ alkanol is used, use of a catalyst can be beneficial. For example, a trace of iodine, bromine, an alkali metal bromide or iodide, or an alkyl bromide or iodide can usefully increase the speed of the reaction. Transition metal catalysts can also be used for this purpose.

In general, the reaction of the substrate, ammonia and alkanol can be effected with good conversion and selectivity. For example, N-methylsuccinimide can be formed from the corresponding anhydride with at least 90 percent selectivity and 100 percent conversion.

In general, the reactants, i.e., substrate and ammonia, are used in about stoichiometric proportions. Too little ammonia results in incomplete conversion and too much ammonia is wasteful and can produce undesirable byproducts. The alkanol can be used in about stoichiometric proportions also, however, it is sometimes convenient to use excess alkanol to aid in introduction and removal of feed and product.

The N-alkyl products are generally easily separated from the reaction mixture because of the high conversions and selectivities. Where product separations are required they may be usefully carried out by distillation or crystallization.

Reduction of the organic substrate together with the ammonolysis-alkylation reaction can be accomplished catalytically by adding hydrogen and a reduction catalyst to the reaction mix. By reduction is meant either reduction of a carbon-carbon double bond or a carbonyl group, or both. Catalysts useful for the heterogeneous reduction reaction are, generally, nickel supported on a metal oxide, copper chromite, cobalt supported on a metal oxide, and other similar catalysts. In general, temperature and pressure ranges are those expected for a reaction of this kind and are consistent with those required for ammonolysis-alkylation. A reduction temperature between about 100° C. and about 500° C., more preferably between about 150° C. and about 300° C., and a reduction pressure of between about 10 atms. and about 600 atms., more preferably between about 20 atms. and about 400 atms. can be used, as can be understood by one skilled in the art. Advantageously, the reaction mixture is agitated by stirring, or otherwise mixed, in order to improve contact between the reactants. Reaction times of course vary with the reaction temperature and pressure used, as may be expected by one skilled in the art, but in general lie between about 1 hr. and about 12 hrs.

The following Examples will serve to illustrate certain specific embodiments of the herein disclosed invention. These Examples should not, however, be construed as limiting the scope of the novel invention as there are many variations which may be made thereon without departing from the spirit of the disclosed invention, as those of skill in the art will recognize.

EXAMPLES

General

All reactions were run in a 300cc 316SS stirred Autoclave Engineer autoclave at the reaction times, temperatures and pressures noted in the Examples below. In addition, a one-gallon autoclave was used for Example 2. Products were analyzed using both liquid chromatography and gas chromatography and all conversion and selectivity percentages given are in mole percent.

In general the substrate, for example, succinic anhydride, and the alcohol were first added to the reactor followed by an argon purge. Ammonia gas was then added, and, optionally hydrogen gas; the autoclave was then sealed and agitation begun. The reactor was heated to reaction temperature, and the reaction time taken to be the time the reactor was held at reaction temperature.

EXAMPLE 1

A 67 g amount of succinic anhydride (SAN), 62 g of methanol, and 12.53 g of ammonia were heated 5 hrs. at 300° C. while stirring at 900 RPM. The SAN was 100% converted and selectivity to N-methylsuccinimide was 90%.

EXAMPLE 2

A 67 g amount of SAN, 89 g of ethanol and 12.53 g of ammonia were heated 5 hrs. at 292° C. while stirring at 900 RPM. The SAN was 100% converted with a 40% selectivity to N-ethylsuccinimide and a 40% selectivity to succinimide.

EXAMPLE 3

A 50 g amount of SAN, 106 g of butanol and 9.4 g of ammonia were heated 22 hours at 300° C. while stirring. The SAN was 100% converted with a 40% selectivity to N-butylsuccinimide and a 40% selectivity to succinimide.

EXAMPLE 4

A 99 g amount of phthalic anhydride (PAN), 65 g of ethanol and 12.5 g of ammonia were heated 22 hrs. at 300° C. while stirring. The PAN was 100% converted with a 91% selectivity to N-ethylphthalimide.

EXAMPLE 5

A 120 cc amount of dimethylsuccinate (DMS) and 32 cc of anhydrous ammonia were heated 2 hours at 300° C. while stirring. The DMS was 100% converted with a 90% selectivity to N-methylsuccinimide.

COMPARISON EXAMPLE 6

A 12 g amount of succinimide and 120 cc of methanol were heated 4 hrs. at 230° C. while stirring. The succinimide was 90% converted with a 40% selectivity to N-methylsuccinimide and a 50% selectivity to DMS.

EXAMPLE 7

A 57.7 g amount of butyrolactone (BL), 50 g of methanol and 12.53 g of ammonia were heated 15 hours at 290° C. while stirring. The BL was 95% converted with a 35% selectivity to N-methylpyrrolidone and a 55% selectivity to pyrrolidone.

EXAMPLE 8 a 79 g amount of succinic acid (SA), 40 g of methanol and 12.53 g of ammonia were heated 3 hrs. at 290° C. while stirring. The SA was 100% converted with a 90% selectivity to N-methylsuccinimide.

EXAMPLE 9

A 60 g amount of SAN, 40 g of methanol, 12.53 g of ammonia, and 4 g of NaI were heated 15 hours at 200° C. while stirring. The SAN was 100% converted with an 80% selectivity to N-methylsuccinimide and a 15% selectivity to succinimide. The same reaction conditions except for elimination of the NaI produced 100% SAN conversion with a 50% selectivity to N-methylsuccinimide and a 40% selectivity to succinimide.

EXAMPLE 10

A 73 g amount of dimethylsuccinate (DMS), 36.6 g of ammonium hydroxide, and 900 psig of hydrogen were heated 16 hrs. at 260° C. over 12 g of a 5% palladium on carbon catalyst while stirring. The DMS was 100% converted with a 70% selectivity to N-methylsuccinimide and a 20% selectivity to N-methylpyrrolidone.

EXAMPLE 11

A 65 g amount of SAN, 41 g of methanol, 12.15 g of ammonia, 12 g of 5% palladium on carbon catalyst, and 700 psig of hydrogen were heated 21 hours at 290° C. while stirring. The SAN was 100% converted with a 60% selectivity to N-methylsuccinimide and a 30% selectivity to N-methylpyrrolidone.

What is claimed is:

1. A process comprising forming a first compound containing the

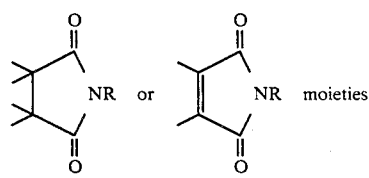

from a second compound containing the

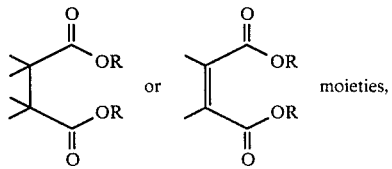

wherein R is H or a $C_1$ to $C_8$ alkyl radical, by contacting under reaction conditions said second compound with ammonia and the corresponding $C_1$ to $C_8$ alkanol.

2. The process of claim 1 wherein said second compound is

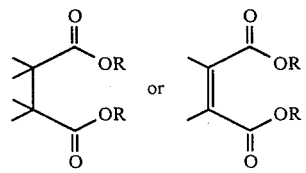

3. The process of claim 2 wherein said R is a $C_1$ to $C_4$ alkyl radical and said alkanol is the corresponding $C_1$ to $C_4$ alkanol.

4. The process of claim 2 wherein said R is the methyl radical and said alkanol is methanol.

5. The process of claim 1 wherein said second compound is

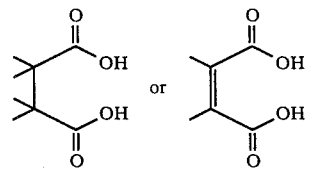

and said R is a $C_1$ to $C_8$ alkyl radical.

6. The process of claim 5 wherein said R is a $C_1$ to $C_4$ alkyl radical and said alkanol is the corresponding $C_1$ to $C_4$ alkanol.

7. The process of claim 5 wherein R is the methyl radical.

8. A process comprising forming a first compound containing the

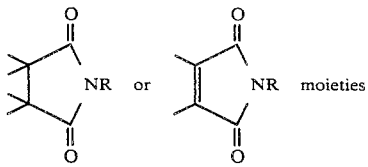 moieties from a second compound containing the

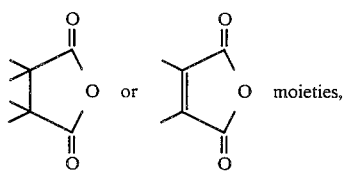 moieties, wherein R is a $C_1$ to $C_8$ alkyl radical, by contacting under reaction conditions said second compound with ammonia and the corresponding $C_1$ to $C_8$ alkanol.

9. The process of claim 8 wherein said second compound is

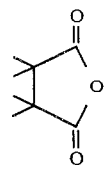

10. The process of claim 9 wherein said R is a $C_1$ to $C_4$ alkyl radical and said alkanol is the corresponding $C_1$ to $C_4$ alkanol.

11. The process of claim 9 wherein said R is the methyl radical and said alkanol is methanol.

12. A process comprising forming N-methylsuccinimide by contacting under reaction conditions succinic acid, ammonia and methanol.

13. A process comprising forming N-methylsuccinimide by contacting under reaction conditions succinic anhydride, ammonia and methanol.

* * * * *